United States Patent [19]

DuFault et al.

[11] Patent Number: 4,721,114

[45] Date of Patent: Jan. 26, 1988

[54] METHOD OF DETECTING P-WAVES IN ECG RECORDINGS

[75] Inventors: Robert A. DuFault, Roseville; Ann C. Wilcox, St. Paul, both of Minn.

[73] Assignee: Cardiac Pacemakers, Inc., St. Paul, Minn.

[21] Appl. No.: 831,519

[22] Filed: Feb. 21, 1986

[51] Int. Cl.$^4$ .............................................. A61B 5/04
[52] U.S. Cl. .................................................. 128/696
[58] Field of Search ................ 128/419 PT, 695, 696, 128/697, 702–704, 707, 708, 710; 364/415, 417

[56] References Cited

U.S. PATENT DOCUMENTS

| | | | |
|---|---|---|---|
| 3,832,994 | 9/1974 | Bicher | 128/702 |
| 3,848,586 | 11/1974 | Suzuki et al. | 128/696 |
| 4,023,564 | 5/1977 | Valiquette et al. | 128/708 |
| 4,038,536 | 7/1977 | Feintuch | 128/696 |
| 4,170,992 | 10/1979 | Dillman | 128/702 |
| 4,211,237 | 7/1980 | Wagel | 364/417 |
| 4,336,810 | 6/1982 | Anderson et al. | 128/702 |
| 4,422,459 | 12/1983 | Simson | 128/702 |
| 4,510,945 | 4/1985 | Barreras | 128/696 |
| 4,552,154 | 11/1985 | Hartlaub | 128/702 |

OTHER PUBLICATIONS

Gcovaerts et al, "IEEE Transactions on Biomedical Engineering", vol. BME 23, No. 2, Mar. 1976, pp. 154–160.

Primary Examiner—William E. Kamm
Attorney, Agent, or Firm—Orrin M. Haugen; Thomas J. Nikolai; Frederick W. Niebuhr

[57] ABSTRACT

A method for automatically detecting P-waves in a continuous electrocardiograph signal stream irrespective of the presence of P-R disassociation wherein the lower energy P-wave can meld into the higher energy R-wave. In accordance with the invention, the ECG signal stream is digitized and fed to a computer programmed to perform signal processing operations thereon. First, a basic QRS morphologic prototype is developed through coherent-averaging of a plurality of QRS complexes appearing in the signal stream. Once the prototype is established, it is aligned with the incoming ECG signal stream where a recognizable similarity exists. The prototype is multiplied by a function comprising a "window" to smooth it to zero at its right and left edges while preserving essential center shape. The resulting windowed prototype is then scaled to match in amplitude or energy content the ECG signal stream at the points of alignment. The thus-modified prototype is then subtracted from the signal stream at those points, forming a residue waveform comprising P-waves, residual R-wave energy and ectopic beats. The residue signal may then be smoothed before comparing it to a predetermined linear threshold. The energy amplitudes in the residue signal exceeding the threshold are identified as P-waves.

2 Claims, 7 Drawing Figures

METHOD OF DETECTING P-WAVES IN ECG RECORDINGS

BACKGROUND OF THE INVENTION

I. Field of the Invention

This invention relates generally to biomedical apparatus, and more specifically to a method and apparatus for locating and identifying P-waves in an ECG signal stream, regardless of the existence of PR disassociation.

II. Discussion of the Prior Art

Assessment and analysis of arrhythmias requiring P-wave detection have long been restricted by the lack of effective P-wave detection algorithms. It is recognized that, in surface electrocardiograms, the ratio of R-wave energy to P-wave energy is typically 20-30 dB. That is, the P-wave energy picked up on the surface of the body will typically have 0.01 to 0.001 of the R-wave energy. Furthermore, the P and R-wave spectra have sufficient overlap that traditional linear filtering techniques do not yield sufficient separability. In this regard, reference is made to Pp. 1,113-1,118 of *Cardiac Pacing Electrophysiology and Pacemaker Technology* containing a chapter entitled "Waveform Analysis of Atrial Electrograms" by A. E. Aubert, et al. Compounding the problem occasioned by the substantial energy difference between P and R-waves and their overlap in the frequency domain is the presence of baseline drift in the ECG signal train and the variety of noise sources which may be encountered during the pickup of the ECG signal stream.

While certain schemes are known for detecting P-waves when such waves are in sinus rhythm with the R-waves, such schemes do not work in the presence of arrhythmias or when the patient's heart is producing disassociated P and R-waves. Here, the P-wave can float into the R-wave and be masked by it.

In a paper by D. E. Gustafson, et al entitled, "A New Technique for Detection of P-Waves" presented at the Midcon Conference on Nov. 6-8, 1979 in Chicago, the authors describe a technique employing the Loeve-Karnunem (L-K) expansion to estimate a noise-free mean QRS complex which is then removed using digital subtraction, from a similar estimate of each QRS complex, leaving a residual signal containing error terms from the L-K approximation, and P-waves. While this process can detect P-waves free of other portions of the cardiac cycle, or proximate to T-waves, it does not work satisfactorily when the P-wave is obscured by the QRS complex. It is conjectured that the L-K reconstruction, fitted term-by-term to the QRS in which a P-wave is contained, allows too many degrees of freedom and thus removes the P-wave energy as well as the R-wave energy during subtraction.

While P-wave detection can be achieved using an esophageal lead or atrial epicardial leads implanted during cardiac surgery for monitoring during critical recovery, these invasive or semi-invasive techniques are generally not acceptable for ambulatory monitoring or for continuous coronary care monitoring where cardiac surgery is not contemplated.

The lack of a reliable non-invasive P-wave detector algorithm has thus hampered development of automatic super-ventricular arrhythmia diagnostic routines, both in ambulatory and coronary care unit monitoring applications. At present, no commercially available computer-based arrhythmia diagnostic systems incorporating atrial activity into the diagnostic logic are available in the marketplace.

Accurate P-wave sensing is required for accurate arrhythmia and tachycardia assessment and for prompt, safe and effective intervention. The current state of the art uses one or the other of the following two methodologies:

1. Using the R-wave as a fiducial point, a search is made, backward in time, to the expected position of the P-wave and a statistical detection technique is used to make a probabilistic determination of the presence or absence of P-wave at that moment. This technique is not suitable for variable, unexpected or disassociated P-R timing relationships.

2. The use of a separate invasive (endocardial or myocardial) or semi-invasive (esophageal lead) to make a separate determination of the P-wave. Such techniques are acceptable only in selected circumstances where the patient incurs little additional stress or discomfort from their presence, but are not acceptable in general, especially in ambulatory Holter monitoring.

SUMMARY OF THE INVENTION

The method of the present invention provides reliable P-wave detection methodology without recourse to or dependence upon specific timing relationships or timing stability between P-wave and R-wave occurrences. Using the method of the present invention, it is possible to detect the P-waves, whether in normal relationship to the R-wave or even when masked by the R-wave. The method described herein applies to ECG signal trains obtained from single surface leads, whether in a coronary care unit or Holter monitor or to unipolar epicardial or endocardial leads located nearly anywhere in the atrium or ventricle.

In carrying out the method, a representative QRS complex is formed, either by selecting an initial QRS prototype for this purpose, or by coherent-averaging of a sufficient number of beats during a "learning phase" of operation. Next, the representative QRS morphologic prototype undergoes centering and multiplication by a suitable window process. The resulting QRS prototype, so treated, is now referred to as the QRS reference complex or template.

The QRS reference is next aligned to each subsequent QRS in the signal train having a similar morphology. The alignment process involves a normalized convolution, using the QRS reference as a finite-impulse response filter in the convolution process. Those local maxima in the output of the normalized convolution output, which are also over a preestablished threshold, serve both as a measure of the alignment and a morphologic similarity. At each alignment point, the QRS reference is scaled, either for the best peak-to-peak match or the best match of energy content, and is then subtracted. Subtraction occurs only from morphologically-similar QRS complexes, the degree of similarity being governed by the threshold value.

Unless there is morphologic identity, some residue will be left by this process, the nature and severity of which can be controlled by proper choice of scaling and windowing parameters applied to the QRS reference before subtraction from the corresponding complexes in the ECG signal stream, and by linear band-pass filtering following the subtraction. Because the subtraction process reduces the R-wave energy by 20-30 dB without affecting appreciably the P-wave energy, a band-pass filter centered on the P-wave spectrum may now be employed to enhance the P-wave relative to the residue and background clutter without the saturation or excessive ringing which would result from similar filtering of the input signal. As those skilled in the signal processing art will realize, at this point the bulk of the R-wave energy has been removed from the signal stream and the result has been filtered, leaving a slightly distorted version of the P-wave, some residual R-wave energy and possibly some R-waves of ectopic origin.

If the P-waves are of reasonable amplitude and predominantly uniphasic following the band-pass filtering operation, they may be directly detected through the use of a linear thresholding technique. All of the processing up to this thresholding, with the various possible parametric trade-offs optimized, constitute a "receiver". Varying the threshold and scoring the resulting variation in detection/false alarm ratio determines a receiver operating characteristic (ROC) curve for this receiver.

Alternatively, if the P-waves, after the band-pass filtering operation, are fairly stable, morphologically, but do not yield, because of morphology or energy, to simple thresholding, then a second convolution process may be used. Here, a P-wave morphologic estimate can be made during a learning interval. This may be used as a reference in a continuous normalized convolution process, just as was the initial R-wave removal technique described above. The convolution values are continuously normalized so that the output function is always between +1 for a perfect match and −1 for an anti-match. The normalization permits very simple threshold implementation. The addition of a second correlator qualifies the combination as a second receiver. Again, its performance is qualified for comparison by varying the threshold to construct a second ROC curve. Standard techniques for comparing receiver performance using ROC curves are well known in the signal processing field.

OBJECTS

Accordingly, it is a principal object of the present invention to provide an improved method for detecting P-waves in surface ECG signal trains.

Another object of the invention is to provide a series of signal processing algorithms executable in a general purpose digital computer for identifying P-waves in a surface ECG signal train.

Another object of the invention is to provide a method for detecting P-wave complexes in a surface ECG signal train where P-R disassociation and/or arrhythmias are present while still detecting during normal sinus rhythm.

These and other objects and advantages of the invention will become apparent to those skilled in the art from the following detailed description of the preferred method, especially when considered in conjunction with the accompanying drawings.

DESCRIPTION OF THE PREFERRED EMBODIMENT

Figure 1:
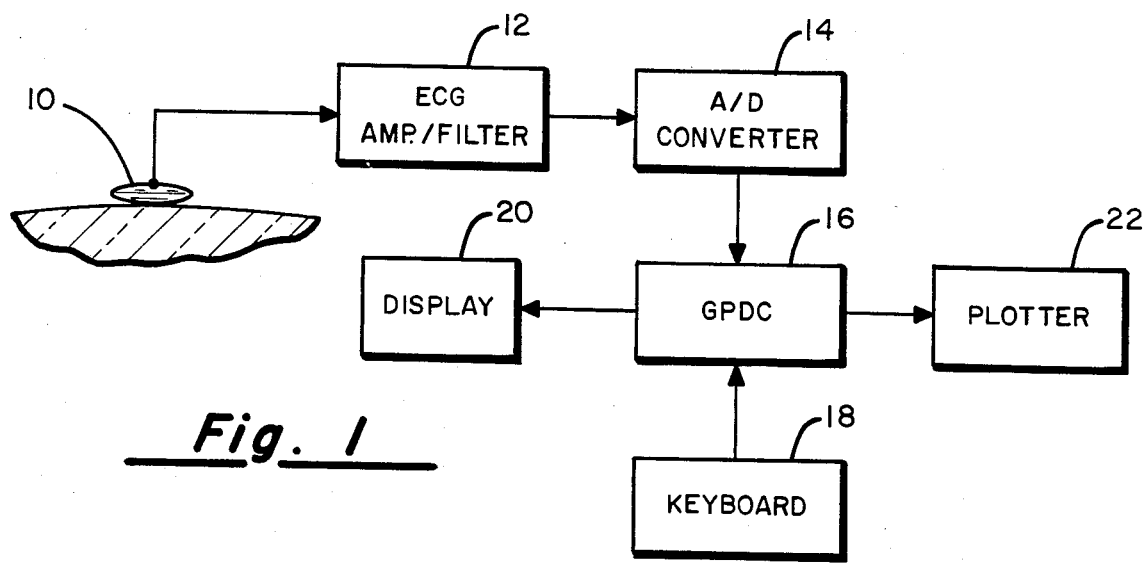
FIG. 1 is a system block diagram of the hardware used in carrying out the method of the present invention.

Referring to FIG. 1, there is illustrated by means of a general block diagram the hardware components used in carrying out the P-wave detection method of the present invention. The system is seen to include an ECG surface electrode 10 which is adapted to be suitably positioned on the chest or other area of a patient's body, and that surface electrode is connected by suitable conductors to the ECG amplifier/filter circuitry 12 which functions to produce an analog signal train corresponding to the ECG pattern being detected. This analog waveform is applied to an analog-to-digital converter 14 wherein the waveform is sampled at a predetermined sampling rate and digital quantities are developed corresponding to the amplitude of the ECG signal at those particular sampling times.

The digital output from the A/D converter is, in turn, fed to a general purpose digital computer (GPDC) 16 where it is at least temporarily stored in the memory associated with that computer so as to be available as operands to be worked upon by a series of instructions comprising the computer's program to carry out a series of steps whereby the P-wve signal contained in the ECG signal stream can be detected. Operator input is provided to the GPDC via a keyboard 18, and the computer provides an output to a visual display device 20 and to a plotter 22 which may be used to give a hardcopy readout of what is being displayed on the CRT screen of the display device 20.

Figure 2:
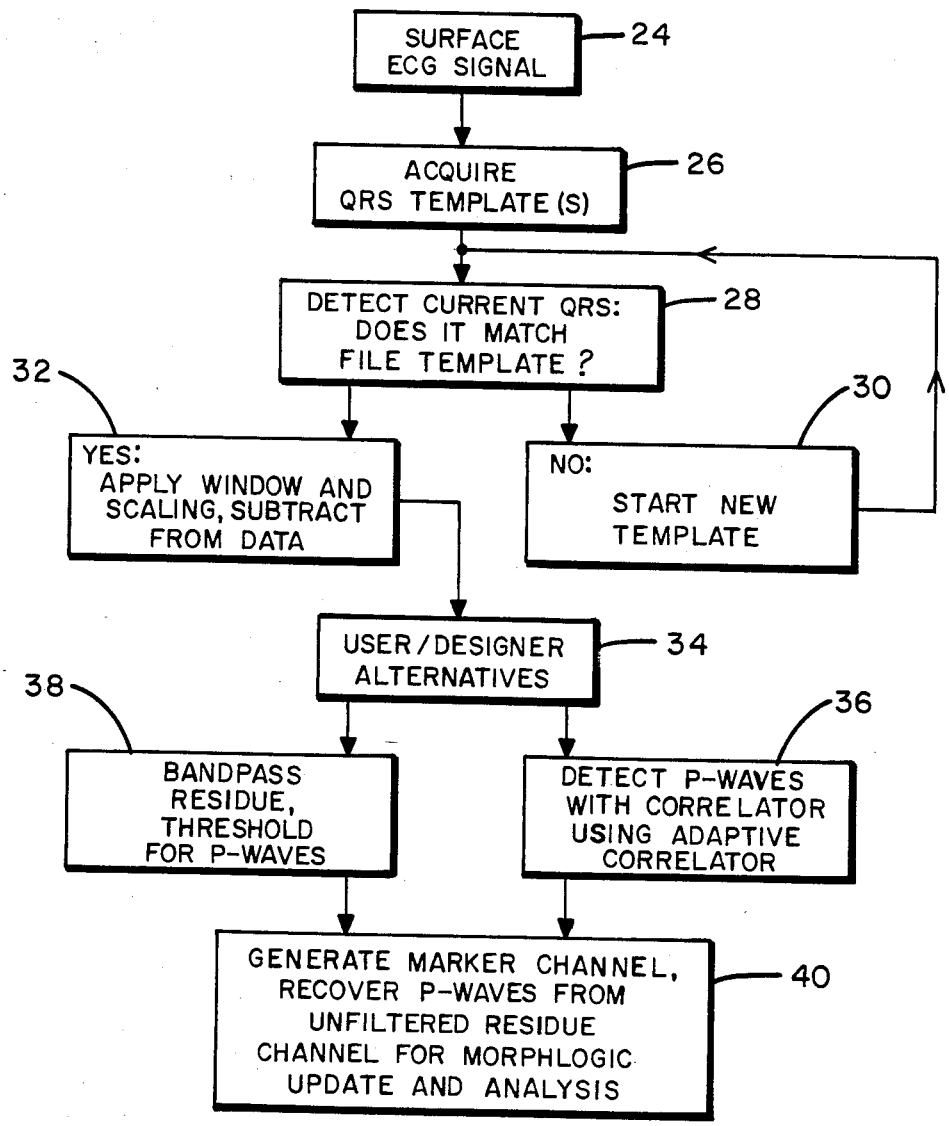
FIG. 2 is a flow diagram indicating the sequence of the various steps carried out by the programmed general purpose digital computer shown in FIG. 1.

FIG. 2 is a flow chart of the P-wave detection method comprising the present invention. Persons of ordinary skill in the field of signal processing and computer programming, having had the benefit of the detailed teachings of the present specification, will be in a position to prepare the machine language coding or a higher level language program to be executed in the computer for carring out the operations indicated in the flow chart of FIG. 2. Hence, it is not deemed necessary to provide the specific instructions comprising the program because those instructions would necessarily depend upon the type of computer employed.

Referring to FIG. 2 then, block 24 represents the operation of obtaining a surface ECG signal train by way of the electrodes 10 and ECG amplifier/filter 12. The function represented by block 26 labeled "ACQUIRE QRS TEMPLATE (S)" is carried out by selecting an initial QRS complex from the ECG signal train or, alternatively, by the coherent-averaging of a sufficient number of such QRS complexes during an initial "learning phase" of operation. The template referred to is actually a reference QRS complex having a predetermined morphology and is obtained by accumulating an ensemble of similar QRS morphologies by way of an adaptive correlator algorithm, executed by the computer, which detects and aligns the ensemble for coherent-averaging. By providing a sufficient sampling duration, a stable morphlogy can result, even in the presence of a variety of arrhythmias, providing the underlying QRS morphology is stable and the P-wave is not phase-locked within the QRS, as it is in 1:1 retrograde conduction.

Once the template has been established, it is matched with the subsequent ECG input signal stream to locate QRS complexes in that signal stream which morphologically match the template, i.e., have highly similar shapes to within a scale factor. Incidences of a suitable match and the time of occurrence of that match are then stored in the computer's memory.

As indicated by block 30, if a sufficiently close match between the template and the current ECG signal train does not result but there is still a sufficient amount of energy in the signal train to suggest that an R-wave may be present, that section of the input signal train is acquired and may be used to begin the formation of a new QRS template which may represent a new family of QRS complexes, such as one containing ventricular tachycardia or ectopic occurrences. Thus, the algorithm used does not depend upon a fixed template, but new templates can be constructed on a real-time basis as changes of a given nature occur in the ECG signal stream being received.

If, however, a good match is established between the template and a current QRS complex, as indicated by block 32, "windowing" and "scaling" operations are performed on the QRS representative morphology prior to the subtraction of the modified prototype from the current QRS complex in the signal train to thereby minimize the QRS energy in the residual signal. More specifically, the "windowing" operation serves to prevent discontinuities in the residue signal following subtraction caused by different baseline levels between the template comprising the morphologic prototype and the signal at the edges of the finite length template which could result in the triggering of false detections. The window function employed must be a compromise between a smooth endpoint transition and minimum distortion of the prototype QRS near the center of the window. It has been found that a useful window for this purpose may be derived from a Hann window:

$$LH_i = \frac{\text{LOG}(1 + \alpha H_i)}{\text{LOG}(1 + \alpha)}$$

Where $H_i$ is the value of the Hann window, $LH_i$ is the value of the derived function and $\alpha$ is a shaping parameter. An $\alpha$ value close to 500 has been found to result in a desired window factor for application to the prototype or template to reduce discontinuities caused by the edge effect.

Those desiring further information concerning the Hann window signal processing technique may refer to Hamming, "Digital Filters", pp. 90–108, Prentice-Hall, 1983.

The windowed QRS template is next aligned to each subsequent QRS complex in the ECG signal stream being received where the morphologies between the two are determined to be sufficiently similar.

The measure of similarity is inherent in the correlator process which yields a figure of similarity of +1 for perfect similarity. A useful alignment process is the signal processing process referred to as normalize convolution, where the QRS windowed template is used as a finite-impulse response filter in the convolution process. Then, the local maxima in the output of the normalized convolution output, which are also over threshold, serve both as a measure of alignment and of morphology similarity. At each alignment point, the window QRS template is scaled, either for the best peak-to-peak match or for the best energy match. Once the scaling has been done, the scaled and windowed template is subtracted from the morphologic-similar QRS complexes where the degree of similarity is governed by a threshold value. Unless there is morphologic identity, some residue will be left by this process. The nature and severity of the residue can, however, be controlled through proper choice of scaling and windowing of the template before subtraction and by linear band-pass filtering following subtraction.

The block 34 in FIG. 2 labeled "User/Designer Alternatives" constitutes a decision point, but is not one that is necessarily under program control. That is to say, the user here decides which of two further computational paths should be pursued. Assuming that it is the path including block 36 that is followed, a further correlator is used for detecting the P-waves in the residue signal in the same fashion that a correlation process has been used initially in detecting R-waves in the ECG signal train. That is to say, an initial P-wave is acquired and used with the correlator process to detect and refine the P-wave estimate while, at the same tme, producing detector indications of where the P-waves occur. The level of performance is dependent on the noise properties of the residue signal which, in turn, depend on the efficacy of QRS removal. Since the residual noise may not be Gaussian, a matched filter may be sub-optimal for P-wave detection in this instance.

The alternative path labeled 38 in FIG. 2 does not use a correlator but, instead, employs a simple band-pass filtering technique for smoothing the residual signal, and this is followed by a thresholding process for the detection of P-waves. Because the subtraction process reduces the R-wave energy by 20–30 dB without appreciably affecting the P-wave energy, the use of a band-pass filter centered on the P-wave spectrum has been found to enhance the P-wave relative to the residue signal and background clutter and without saturation or excessive ringing which becomes difficult to achieve when a R-wave is present.

Irrespective of whether path 36 or path 38 is followed, the next operation indicated in the block diagram of FIG. 2 is to generate a marker channel which may be displayed on the cathode ray tube 20 or on the plotter 22 in FIG. 1 as a series of pulses which indicate where the process has resulted in the detection of P-waves. This pulse pattern would normally be shown in conjunction with the input ECG signal so that a trained observer might compare the two to see how the detection marks correspond with any visual indications of P-waves in the ECG signal train.

Operation block 40 in FIG. 2 also indicates that the P-waves may be recovered from the unfiltered residue channel or from the original ECG wave in order to improve the P-wave morphologic estimate or for physiologic or medical analysis of the P-wave morthology. That is, since the filtering technique results in P-wave distortion for purposes of detection, the detection may now be used to recover the undistorted P-wave prior to filtering for purposes of further analysis.

Figure 3A:
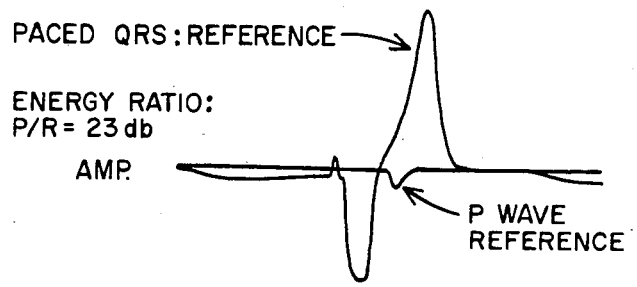
FIGS. 3(a) through 3(e) illustrate the wave shapes produced at various stages of execution of the processes set out in the flow diagram of FIG. 2.

Referring to FIG. 3(a), there is illustrated a composite QRS reference morphology (template) developed through the aforementioned coherent averaging of a plurality of QRS complexes appearing in the ECG signal stream. For purposes of illustration, that QRS reference is overlaid on the graph in FIG. 3(a) with a P-wave template, also developed using coherent averaging, but on the residue following the removal of the R-wave. This figure serves to illustrate why it is difficult to detect P-waves in the ECG signal stream when, due to disassociation, the P-wave merges with the R-wave where the energy difference is approximateely −23 db.

Figure 3B:
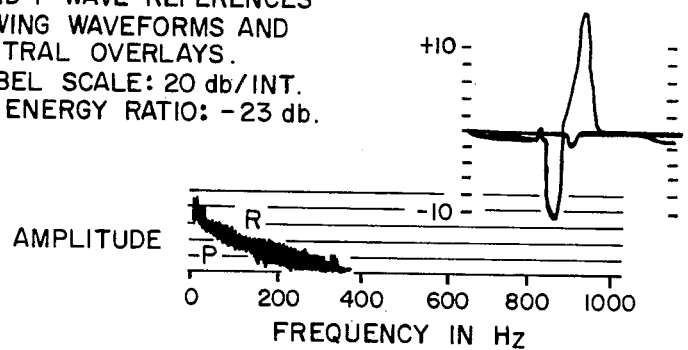

FIG. 3(b) is included to illustrate why a simple band-pass filter cannot be used to separate the P-wave from the R-waves in the original signal. FIG. 3(b) shows a plot of the log of the amplitude of the R-wave and P-wave overlaid with one another. The upper trace shows the R-wave spectrum on a logarithmic scale and located directly beneath it is the P-wave spectrum. In that the two basically contain the same frequency components, one cannot be separated from the other using a straight-forward filtering technique.

Figure 3C:
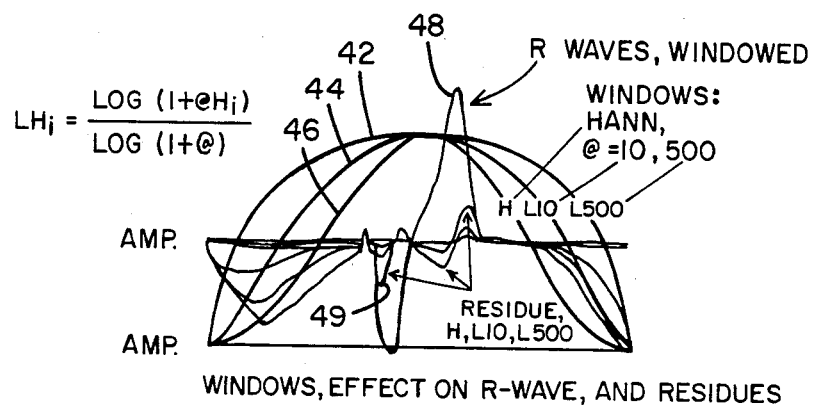

FIG. 3(c) is a composite set of curves illustrating the effects of "windowing" and "scaling" on the R-wave prior to subtraction and how different strategies affect the residue signal. Curves 42, 44 and 46 which extend the full width of the plot are labeled H, L10 and L500, respectively, and depict different window shapes, all of which have unity gain at the center and zero gain at the edges and tapering smoothly to zero. Curve 46 is a Hann window and it is seen to have the effect of altering the leading and trailing edges of the R-wave 48 which is centered in such a fashion that when the R-wave prototype is subtracted from the unwindowed R-wave, certain levels of residue signal result. Numeral 49 identifies the level of residue when the Hann window 46 is utilized. Curves 42 and 44 result in somewhat lower residue values By selecting the appropriate windowing factor, the residue can be minimized while still preventing discontinuities at the edges of the ECG signal train following subtraction of the windowed QRS prototype.

Figure 3D:
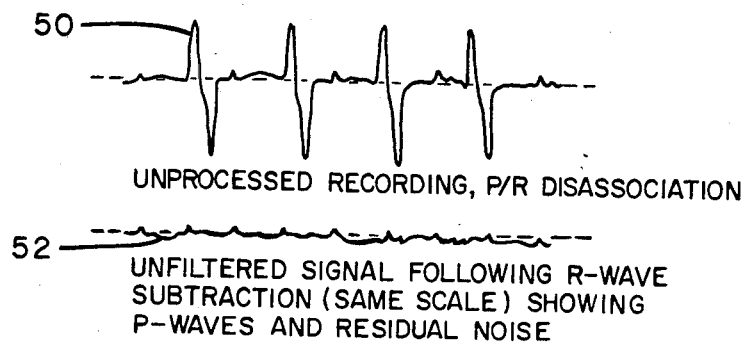
Figure 3E:
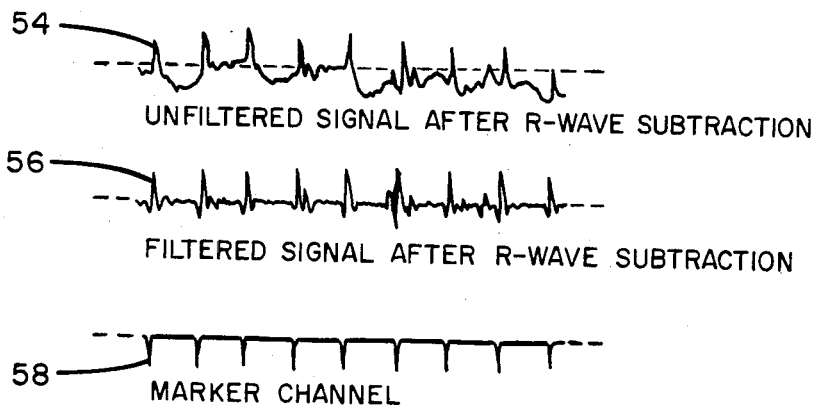

FIG. 3(d) illustrates by way of curve 50 a section of the continuous ECG signal train input signals showing R-waves and P-waves disassociated and intermingled. The waveform 52 comprises the unfiltered signal following the subtraction of the R-wave prototype at the same scale value but before any filtering. This curve shows the P-waves and residual noise. The curve 50 and 52 of FIG. 3(d) are to be compared with curves 54 and 56 in FIG. 3(e). In FIG. 3(e) there is shown the residual signal following R-wave subtraction, but before filtering (curve 54). Curve 56 illustrates the same signal but following the application of band-pass filtering which serves to suppress the residual signal to make the P-waves more prominent. The waveform 58 constitutes the results when the signal train of 56 is thresholded and clearly shows the time of occurrence of the P-waves even though they were originally masked by the R-waves in the ECG signal train.

It is seen, then, that the method of the present invention allows an analysis of the P-R timing relationships obtained from Holter recordings of ventricular-paced patients, in which the ventricular pacing rate is not identical with the atrial rate. Thus, A-V asynchrony may be constantly present and with constantly changing differential rates. While still allowing reliable P-wave detection. This allows P-wave detection of Holter recordings exhibiting P-R disassociation and this is true irrespective of whether there is a normal P-R separation or when the Pwave is masked by the R-wave. Also, this detection is accomplished without recourse to or dependence upon specific timing relationships or timing stability between the P-wave and the R-wave occurrences.

The technique described herein has been implemented, for research purposes, as a multi-pass operation on a general purpose digital computer. As those skilled in the art will recognize, the method described herein may also be implemented as a non-implantable breadboard device, using single pass cascaded operations over a restricted but sufficient band width and can be designed for real-time capability using off-the-shelf components.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished without departing from the scope of the invention itself.

What is claimed is:

1. A method for automatically detecting P-waves in a continuous electrocardiograph (ECG) signal stream, irrespective of the presence of P-R disassociation, comprising the steps of:
   (a) converting said ECG signal stream to a digital representation;
   (b) adaptively developing from the digitized ECG signal stream at least one basic QRS morphologic prototype by the coherent averaging of a number of QRS complexes in said ECG signal stream;
   (c) aligning said basic QRS prototype with similar QRS complexes in said ECG signal stream by a normalized convolution process;
   (d) multiplying said basic QRS prootype by a mathematical window function for tapering said prototype smoothly to zero at its respective edges while preserving its essential shape at the center;
   (e) scaling the windowed QRS prototype to provide an amplitude/energy match with said signal stream at the points of alignment;
   (f) subtracting the scaled and windowed prototype from said signal stream at the points of alignment to form a residue waveform signal principally made up of P-waves, residual R-wave energy and ectopic beats;
   (g) smoothing said residue signal with a linear band pass filter; and
   (h) comparing said residue signal to a predetermined linear threshold, the energy amplitudes in said residue signal exceeding said threshold being idenified as P-waves.

2. A method for automatically detecting P-waves in a continuous electrocardiograph (ECG) signal stream, irrespective of the presence of P-R disassociation, comprising the steps of:
   (a) converting said ECG signal stream to a digital representation;
   (b) adaptively developing from the digitized ECG signal stream at least one basic QRS morphologic prototype by the coherent averaging of a number of QRS complexes in said ECG signal stream;
   (c) aligning said basic QRS prototype with similar QRS complexes in said ECG signal stream;
   (d) multiplying said basic QRS prototype by a mathematical window function for tapering said prototype smoothly to zero at its respective edges while preserving its essential shap at the center;
   (e) scaling the windowed QRS prototype to provide an amplitude/energy match with said signal stream at the points of alignment;
   (f) subtracting the scaled and windowed prototype from said signal stream at the points of alignment to form a residue waveform signal principally made up of P-waves, residual R-wave energy and ectopic beats;
(g) developoing a P-wave morphologic prototype by coherent-averaging of P-waves, predetermined to be morphologically characteristic of P-waves in said residual signal;
(h) developing a normalized correlation function between said residue waveform of step (f) and said P-wave morphologic prototype of step (g); and
(i) detecting the P-waves by applying a predetermined threshold to the normalized correlation function of step (h) whereby the largest positive excursions mark the location of the P-waves.

* * * * *